(12) United States Patent
Stahmann et al.

(10) Patent No.: US 7,945,325 B2
(45) Date of Patent: *May 17, 2011

(54) PACING AND SENSING VECTORS

(75) Inventors: Jeffrey E. Stahmann, Ramsey, MN (US); Bruce Tockman, Scandia, MN (US); Randy Westlund, Minneapolis, MN (US); Rene H. Wentkowski, Overijse (BE); Russell E. Anderson, Marine on St. Croix, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1079 days.

This patent is subject to a terminal disclaimer.

(21) Appl. No.: 11/554,146

(22) Filed: Oct. 30, 2006

(65) Prior Publication Data
US 2007/0055313 A1 Mar. 8, 2007

Related U.S. Application Data

(63) Continuation of application No. 09/779,754, filed on Feb. 8, 2001, now Pat. No. 7,130,682.

(51) Int. Cl.
*A61N 1/362* (2006.01)
(52) U.S. Cl. ............................................. 607/9; 607/15
(58) Field of Classification Search .................. 607/9, 15
See application file for complete search history.

(56) References Cited

U.S. PATENT DOCUMENTS

| | | | |
|---|---|---|---|
| 3,915,174 A | 10/1975 | Preston | |
| 4,117,848 A | 10/1978 | Naylor | |
| 4,248,238 A | 2/1981 | Joseph | |
| 4,497,326 A | 2/1985 | Curry | |
| 4,558,702 A | 12/1985 | Barreras et al. | |
| 4,603,705 A | 8/1986 | Speicher et al. | |
| 4,628,934 A | 12/1986 | Pohndorf et al. | |
| 4,628,943 A | 12/1986 | Miller | |
| 4,641,656 A | 2/1987 | Smits | |

(Continued)

FOREIGN PATENT DOCUMENTS
DE 19930264 12/2000

OTHER PUBLICATIONS

Agren, M S., et al., "Collagenase During Burn Wound Healing: Influence of a Hydrogel Dressing and Pulsed Electrical Stimulation", *Plast. Reconstr. Surg.*. 94,(1994),518-24.

(Continued)

*Primary Examiner* — Kennedy J Schaetzle
(74) *Attorney, Agent, or Firm* — Schwegman, Lundberg & Woessner, P.A.

(57) ABSTRACT

A method for allowing cardiac signals to be sensed and pacing pulse vectors to be delivered between two or more electrodes. In one embodiment, cardiac signals are sensed and pacing pulse vectors are delivered between at least one of a first left ventricular electrode and a second left ventricular electrode. Alternatively, cardiac signals are sensed and pacing pulse vectors are delivered between different combinations of the first and second left ventricular electrodes and a first supraventricular electrode. In addition, cardiac signals are sensed and pacing pulse vectors are delivered between different combinations of the first and second left ventricular electrode, the first supraventricular electrode and a conductive housing. In an additional embodiment, a first right ventricular electrode is used to sense cardiac signals and provide pacing pulses with different combinations of the first and second left ventricular electrodes, the first supraventricular electrode and the housing.

24 Claims, 10 Drawing Sheets

U.S. PATENT DOCUMENTS

| | | | |
|---|---|---|---|
| 4,708,145 | A | 11/1987 | Tacker, Jr. et al. |
| 4,741,342 | A | 5/1988 | Stotts |
| 4,745,923 | A | 5/1988 | Winstrom |
| 4,819,661 | A | 4/1989 | Heil, Jr. et al. |
| 4,821,723 | A | 4/1989 | Baker, Jr. et al. |
| 4,858,610 | A | 8/1989 | Callaghan et al. |
| 4,858,623 | A | 8/1989 | Bradshaw et al. |
| 4,913,164 | A | 4/1990 | Greene et al. |
| 4,928,688 | A | 5/1990 | Mower |
| 5,050,601 | A | 9/1991 | Kupersmith et al. |
| 5,087,243 | A | 2/1992 | Avitall |
| 5,190,052 | A | 3/1993 | Schroeppel |
| 5,243,978 | A | 9/1993 | Duffin, Jr. |
| 5,265,602 | A | 11/1993 | Anderson et al. |
| 5,269,319 | A | 12/1993 | Schulte et al. |
| 5,281,219 | A | 1/1994 | Kallok |
| 5,311,966 | A | 5/1994 | Daniels |
| 5,314,430 | A | 5/1994 | Bardy |
| 5,324,309 | A | 6/1994 | Kallok |
| 5,328,442 | A | 7/1994 | Levine |
| 5,330,506 | A | 7/1994 | Alferness et al. |
| 5,331,966 | A | 7/1994 | Bennett et al. |
| 5,336,253 | A | 8/1994 | Gordon et al. |
| 5,344,429 | A | 9/1994 | Smits |
| 5,370,665 | A | 12/1994 | Hudrlik |
| 5,385,574 | A | 1/1995 | Hauser et al. |
| 5,391,200 | A | 2/1995 | KenKnight et al. |
| 5,403,356 | A | 4/1995 | Hill et al. |
| 5,405,375 | A | 4/1995 | Ayers et al. |
| 5,411,528 | A | 5/1995 | Miller et al. |
| 5,423,873 | A | 6/1995 | Neubauer et al. |
| 5,431,681 | A | 7/1995 | Helland |
| 5,466,254 | A | 11/1995 | Helland |
| 5,487,758 | A | 1/1996 | Hoegnelid et al. |
| 5,501,702 | A | 3/1996 | Plicchi et al. |
| 5,501,703 | A | 3/1996 | Holsheimer et al. |
| 5,507,781 | A | 4/1996 | Kroll et al. |
| 5,531,764 | A | 7/1996 | Adams et al. |
| 5,571,163 | A | 11/1996 | Helland |
| 5,584,865 | A | 12/1996 | Hirschberg et al. |
| 5,634,899 | A | 6/1997 | Shapland et al. |
| 5,649,966 | A | 7/1997 | Noren et al. |
| 5,720,768 | A | 2/1998 | Verboven-Nelissen |
| 5,766,230 | A | 6/1998 | Routh et al. |
| 5,792,203 | A | 8/1998 | Schroeppel |
| 5,792,208 | A | 8/1998 | Gray |
| 5,797,967 | A | 8/1998 | KenKnight |
| 5,800,464 | A | 9/1998 | Kieval |
| 5,800,465 | A | 9/1998 | Thompson et al. |
| 5,814,079 | A | 9/1998 | Kieval |
| 5,836,981 | A | 11/1998 | Chang et al. |
| 5,843,132 | A | 12/1998 | Ilvento |
| 5,861,013 | A | 1/1999 | Peck et al. |
| 5,895,416 | A | 4/1999 | Barreras et al. |
| 5,928,269 | A | 7/1999 | Alt |
| 5,935,160 | A | 8/1999 | Auricchio et al. |
| 5,978,705 | A | 11/1999 | KenKnight et al. |
| 5,995,870 | A | 11/1999 | Cazeau et al. |
| 5,999,849 | A | 12/1999 | Gord et al. |
| 5,999,853 | A | 12/1999 | Stoop et al. |
| 6,002,962 | A | 12/1999 | Huang et al. |
| 6,047,211 | A | 4/2000 | Swanson et al. |
| 6,067,470 | A | 5/2000 | Mower |
| 6,070,100 | A | 5/2000 | Bakels et al. |
| 6,081,748 | A | 6/2000 | Struble et al. |
| 6,085,118 | A | 7/2000 | Hirschberg et al. |
| 6,094,596 | A | 7/2000 | Morgan |
| 6,104,953 | A | 8/2000 | Leyde |
| 6,115,630 | A | 9/2000 | Stadler et al. |
| 6,178,351 | B1 | 1/2001 | Mower |
| 6,185,459 | B1 | 2/2001 | Mehra et al. |
| 6,219,579 | B1 | 4/2001 | Bakels et al. |
| 6,219,582 | B1 | 4/2001 | Hofstad et al. |
| 6,223,079 | B1 | 4/2001 | Bakels et al. |
| 6,223,082 | B1 | 4/2001 | Bakels et al. |
| 6,233,487 | B1 | 5/2001 | Mika et al. |
| 6,238,420 | B1 | 5/2001 | Bakels et al. |
| 6,240,313 | B1 | 5/2001 | Esler |
| 6,275,730 | B1 | 8/2001 | KenKnight et al. |
| 6,282,444 | B1 | 8/2001 | Kroll et al. |
| 6,292,693 | B1 | 9/2001 | Darvish et al. |
| 6,295,470 | B1 | 9/2001 | Mower |
| 6,317,632 | B1 | 11/2001 | Krig et al. |
| 6,337,995 | B1 | 1/2002 | Mower |
| 6,341,234 | B1 | 1/2002 | Thong et al. |
| 6,343,232 | B1 | 1/2002 | Mower |
| 6,366,808 | B1 | 4/2002 | Schroeppel et al. |
| 6,370,427 | B1 | 4/2002 | Alt et al. |
| 6,400,992 | B1 | 6/2002 | Borgersen et al. |
| 6,456,878 | B1 | 9/2002 | Yerich et al. |
| 6,493,582 | B1 | 12/2002 | Ripart et al. |
| 6,539,260 | B1 | 3/2003 | Schloss |
| 6,556,873 | B1 | 4/2003 | Smits |
| 6,574,512 | B1 | 6/2003 | Zhang et al. |
| 6,584,362 | B1 | 6/2003 | Scheiner et al. |
| 6,587,721 | B1 | 7/2003 | Prutchi et al. |
| 6,640,135 | B1 | 10/2003 | Salo et al. |
| 6,735,472 | B2 | 5/2004 | Helland |
| 6,738,669 | B1 | 5/2004 | Sloman et al. |
| 6,788,971 | B1 | 9/2004 | Sloman et al. |
| 7,130,682 | B2 * | 10/2006 | Stahmann et al. ............ 607/9 |
| 2002/0015193 | A1 | 2/2002 | Tabata |
| 2002/0068959 | A1 | 6/2002 | Warren et al. |
| 2002/0077669 | A1 * | 6/2002 | Lindh et al. ............ 607/27 |
| 2002/0151938 | A1 | 10/2002 | Corbucci |
| 2007/0049978 | A1 | 3/2007 | Stahmann et al. |

OTHER PUBLICATIONS

Akyurekli, Y, et al., "Myocardial Responses to Sutureless Epicardial Lead Pacing", *Proc. Vlth World Symp. Cardiac Pacing*, Montreal, Meere, C., ed., *PACESYMP*, chap 33, No. 3, (1979).

Alvarez, O M., et al., "The Healing of Superficial Skin Wounds is Stimulated by External Electric Current", *J. Invest. Dermatol.*, 81, (1983),144-8.

Assimacopoulos, A , et al., "Wound Healing Pomotion by the Use of Negative Electric Current", *Amer. Surg.*, 34, (1968),423-31.

Bassett, C A., et al., "Effect of Electric Current on Bones", In vivo, *Nature*, 204, (1964),65204.

Bassett, C A., et al., "Noninvasive Methods for Stimulating Osteogenesis", *J. Biomed. Mater. Res*, 9, (1975),3714.

Bourguignon, G J., et al., "Electric Stimulation of Proteins and DNA Synthesis in Human Fibroblasts", *FASEB J.*, 1, (1987),398-402.

Burr, H S., et al., "Bio-electric Correlates of wound Healing", *11 Yale J. Biol*, (1938),103-7.

Carley, P J., et al., "Electrotherapy for Acceleration of Wound Healing: Low Intensity Direct Current", *Arch. Phys. Med. Rehabil.*, 66, (1985),443-6.

Cazeau, S , et al., "Four Chamber Pacing in Dilated Cardiomyopathy", *PACE*, 17(Part II), (Nov. 1994),1974-1979.

Chakkalakal, D A., et al., "Electrophysiology of DirecCurrent Stimulation of Fracture Healing in Canine Radium", *IEEE Trans. Biomed. Eng.*, 37, (1990),1048-58.

Daubert, Claude , "Permanent dual atrium pacing in major interatrial conduction blocks: a four years experience (Abstract 141)", *Pacing and clinical electrophysiology : PACE*, 3(Part II), NASPE Abstracts—Abstract 141,(Apr. 1993),885.

Daubert, J C., et al., "Permanent left ventricular pacing with transvenous leads inserted into the coronary veins", *PACE*, 21(Part II), (Jan. 1998),239-245.

Daubert, Claude , "Renewal of permanent left atrial pacing via the coronary sinus", *Pacing and clinical electrophysiology : PACE*, 25(Part II), NASPE Abstracts—Abstract 255,(Apr. 1992),572.

Decaprio, V , et al., "A Comparison of Unipolar and Bipolar Electrograms os Cardiac Pacemaker Sensing", *Circ.*, 56, (1977),750-5.

Dunn, M , et al., "Wound Healing using a Collagen Matrix: Effects of DC Electrical Stimulation", *J. Biomed. Mater. Res.*, 22, (1988),191-206.

Guidant, "CONTAK TR CHFD Model 1241", *System Guide*, Congestive Heart Failure Device,(1999),1-191.

Jiang, H , "Acceleration of Epidermis Proliferation by Direct Current Stimulation", *Chung Hua Cheng Hsing Shao Shang, 8, Abstract Only.*, (1992),136-8.

Kay, G N., "Cardiac Pacing, Practical Cardiac Diagnosis", *2nd ed., Ellenbogen, K.A., ed., Balckwell Science*, Cambridge, MA, (1996),62-65.

Kloth, L C., et al., "Acceleration of Wound Healing with High Voltage, Monophasic, Pulsed Current, Physical Therapy, 68", (1988),503-8.

Konikoff, J J., "Electrical Promotion of Soft Tissue Repairs", *Ann. Biomed. Eng.* 4, (1976),1-5.

Medtronic, "INSYNC III Device Model 8042", *Device Programming Guide*, INSYNC III Device Model 8042, Vision Programmer Software Model 9981,(2000),1-260.

Medtronic, "INSYNC III Device Model 8042", *Device Reference Guide*, INSYNC III Device Model 8042, Vision Programmer Software Model 9981,(2002),1-252.

Mitamura, H , et al., "Importance of the pacing mode in the initiation of ventricular tachyarrhythmia in a canine model of chronic myocardial infarction", *J Am Coll Cardiol.*, 6(1), (Jul. 1985),99-103.

Roy, O Z., et al., "Electrical and Pathological Observations on the Response of the Canine Heart to Cardiac Pacing", *Br. J. Surg.*, 55, (1968),861-2.

Salman, N N., et al., "The Effect of Direct Electric Current Stimulation on the Bone/Porous Metallic Implant Interface", *Biometarials*, 1, (1980),209-13.

St. Jude Medical, "Atlas + HF Models V-343, V-341", *User's Manual*, Implantable Cardioverter-Defibrillator,(Sep. 2003),1-30.

St. Jude Medical, "Epic HF Model V-339", *User's Manual*, Implantable Cardioverter-Defibrillator,(Jul. 2002),1-26.

St. Jude Medical, "Model 3510 Programmer with Model 3307 Software", *Reference Manual*, For Atlas, Atlas+, Epic, Epic+, Photon µ and Photon Implantable Cardioverter/Defibrillators,(Sep. 2003),1-314.

Steinhaus, David M., et al., "Anodal Stimulation: A Potential Concern with Biventricular Pacing?", *PACE*, vol. 24, 553, (Apr. 2001),3 pgs.

Stevenson, W G., et al., "Contribution of the anode to ventricular excitation during bipolar programmed electrical stimulation", *J. Am J Cardiol.*, 57(8), (Mar. 1, 1986),582-6.

Thakral, A , et al., "Effects of anodel vs. cathodal pacing on the mechanical performance of the isolated rabbit heart", *J. Appl Physiol.*, 89(3), (Sep. 2000),1159-64.

Townsend, J F., "Tissue and Electrode Changes in Chronic Cardiac Pacing—An Experimental Study", vol. XI *Trans. Amer. Soc. Artif. Int. Organs*, (1965),132-138.

Varriale, P , et al., "The Ventricular Electrogram", *Chap. 5 in Modern Cardiac Pacing, S.S. Barold, ed., Futura Publ. Co.*, Mount Kisco, NY, (1985).

Weiss, D S., et al., "Exogenous Electric Current can Reduce the Formation of Hypertrophic Scars", *J. Dermatol Surg. Oncol.* 15, (1989),1272-5.

"European Application Serial No. 01988362.8, Office Action mailed Dec. 9, 2008", 4 pgs.

"U.S. Appl. No. 11/554,135, Final Office Action mailed Dec. 10, 2010", 7 pgs.

* cited by examiner

PACING AND SENSING VECTORS

CROSS REFERENCE TO RELATED APPLICATION(S)

This application is a continuation of U.S. patent application Ser. No. 09/779,754, filed on Feb. 8, 2001, now issued as U.S. Pat. No. 7,130,682, the specification of which is incorporated herein by reference.

TECHNICAL FIELD

The present invention relates to implantable medical devices, and more particularly to sensing and delivering energy pulses to and from the coronary vasculature.

BACKGROUND

Cardiac pulse generator systems include a battery powered pulse generator and one or more leads for delivering pulses to the heart. Current pulse generators include electronic circuitry for determining the nature of an irregular rhythm, commonly referred to as arrhythmia, and for timing the delivery of a pulse for a particular purpose. The pulse generator is typically implanted into a subcutaneous pocket made in the wall of the chest. Insulated wires called leads attached to the pulse generator are routed subcutaneously from the pocket to the shoulder or neck where the leads enter a major vein, usually the subclavian vein. The leads are then routed into the site of pacing, usually a chamber of the heart. The leads are electrically connected to the pulse generators on one end and are electrically connected to the heart on the other end. Electrodes on the leads provide the electrical connection of the lead to the heart. The leads are used to sense cardiac signals from the heart and to deliver electrical discharges from the pulse generator to the heart.

The electrodes are typically arranged on a lead body in two ways or categories. A pair of electrodes which form a single electrical circuit (i.e., one electrode is positive and one electrode is negative) positioned within the heart is a bipolar arrangement. The bipolar arrangement of electrodes requires two insulated wires positioned within the lead. When one electrode is positioned in or about the heart on a lead and represents one pole and the other electrode representing the other pole is the pulse generator housing, this arrangement is known as a unipolar arrangement. The unipolar arrangement of electrodes requires one insulated wire positioned within the lead.

In general, the heart can be divided into two sides, a right side and a left side. Each side serves a specific function. The right side of the heart receives blood from the body and pumps it into the lungs to exchange gases. The left side of the heart receives the oxygenated blood from the lungs and pumps it to the brain and throughout the body.

Typically, pacing and defibrillation leads are positioned within the right chambers of the heart, or positioned within the coronary vasculature so as to position one or more electrodes adjacent a left ventricular region of the heart. From their positions within or adjacent to the ventricular chambers, the electrodes on the leads are used to sense cardiac signals and to deliver energy pulses in either a bipolar or a unipolar fashion. This sensing and pacing, however, is accomplished only within or across the chamber in which the lead is implanted. Thus, there exists a need in the art for providing additional options in sensing and delivering electrical energy pulses to a patient's heart.

SUMMARY

The present subject matter provides for an apparatus and method for allowing cardiac signals to be sensed and pacing pulse vectors to be programmed for being delivered between two or more electrodes. In one embodiment, the present subject matter allows for cardiac signals to be sensed and pacing pulse vectors to be delivered between at least one of a first left ventricular electrode and a second left ventricular electrode in a left ventricular region. In an additional embodiment, cardiac signals are sensed and pacing pulse vectors are delivered between different combinations of the first and/or second left ventricular electrodes in a left ventricular region and a first supraventricular electrode in a right atrial region. In addition, cardiac signals are sensed and pacing pulse vectors are delivered between different combinations of the first and/or second left ventricular electrodes in a left ventricular region and a right ventricular electrode in a right ventricular region. In addition, the housing of the apparatus is conductive so as to allow cardiac signals to be sensed and pacing pulse vectors to be delivered between different combinations of the first and second left ventricular electrodes, the first supraventricular electrode, the right ventricular electrode and the housing.

In one embodiment, the apparatus includes an implantable pulse generator to which is attached a first lead and a second lead. The first lead includes a first supraventricular electrode adapted to be positioned in a right atrial region, and the second lead includes the first and second left ventricular electrodes that are both adapted to be positioned adjacent a left ventricular region. The electrodes on the first and second leads are coupled to the implantable pulse generator and to control circuitry within the implantable pulse generator. In one embodiment, the control circuitry includes a pacing output circuit that is programmable to control delivery of pacing pulses between combinations of the first and/or second left ventricular electrodes in the left ventricular region and the first supraventricular electrode in the right atrial region. In an additional embodiment, the pacing output circuit is programmable to control delivery of pacing pulses between combinations of the first and/or second left ventricular electrodes in the left ventricular region and the right ventricular electrode in the right ventricular region.

Examples of the pacing vectors include delivering pacing pulses from the first left ventricular electrode as a cathode to the first supraventricular electrode as an anode. Alternatively, pacing pulses are delivered from the first and/or second left ventricular electrode as a cathode to the right ventricular electrode as an anode. In addition, the pacing output circuit delivers the pacing pulse between the first left ventricular electrode and the second left ventricular electrode in a left ventricular region and the first supraventricular electrode. In addition, the control circuitry includes an extended bipolar cross chamber sensor that receives a cardiac signal sensed between the first left ventricular electrode and the first supraventricular electrode. Alternatively, the cardiac signal is sensed between the second left ventricular electrode and the first supraventricular electrode. Cardiac signals sensed between other combinations of the electrodes, including electrodes in the right ventricle, are also possible.

In one embodiment, the first lead further includes a right ventricular electrode adapted to be positioned in a right ventricular region. Cardiac signals are sensed and pacing pulse vectors are delivered from various combinations of the right ventricular electrode, the first supraventricular electrode, the first and second left ventricular electrodes and the housing. For example, the control circuitry directs the pacing output circuit to deliver pacing pulses from the first left atrial electrode as an anode to the right ventricular electrode as a cathode. Alternatively, the pacing output circuit controls delivery of pacing pulses between the first left ventricular electrode, or the second left ventricular electrode and the conductive housing. In an additional embodiment, the pacing output circuit controls delivery of pacing pulses between the first left ventricular electrode and the second left ventricular electrode and the right ventricular electrode, where the first and second left ventricular electrodes are common. Alternatively, the pacing output circuit controls delivery of pacing pulses between the first left ventricular electrode and the second left ventricular electrode and the right ventricular electrode and the housing of the implantable pulse generator, where the first and second left ventricular electrodes are common and the right ventricular electrode and the housing are common. In addition, the control circuitry allows for a cardiac signal to be sensed between one of the first and second electrodes and the right ventricular electrode and for pacing pulses to be delivered between one, or both, of the first and second electrodes and the right ventricular electrode.

Other combinations of sensing and pacing vectors are possible, as will be more fully described below.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Traditional pacemakers allow for pacing and sensing vectors from within single cardiac chambers. These vectors are typically referred to as "unipolar" and "bipolar", depending upon the relative proximity of the electrodes being used in the pacing and/or sensing. Unipolar and/or bipolar sensing and pacing can be performed within either the atrial chambers or the ventricular chambers of the heart.

Figure 1:
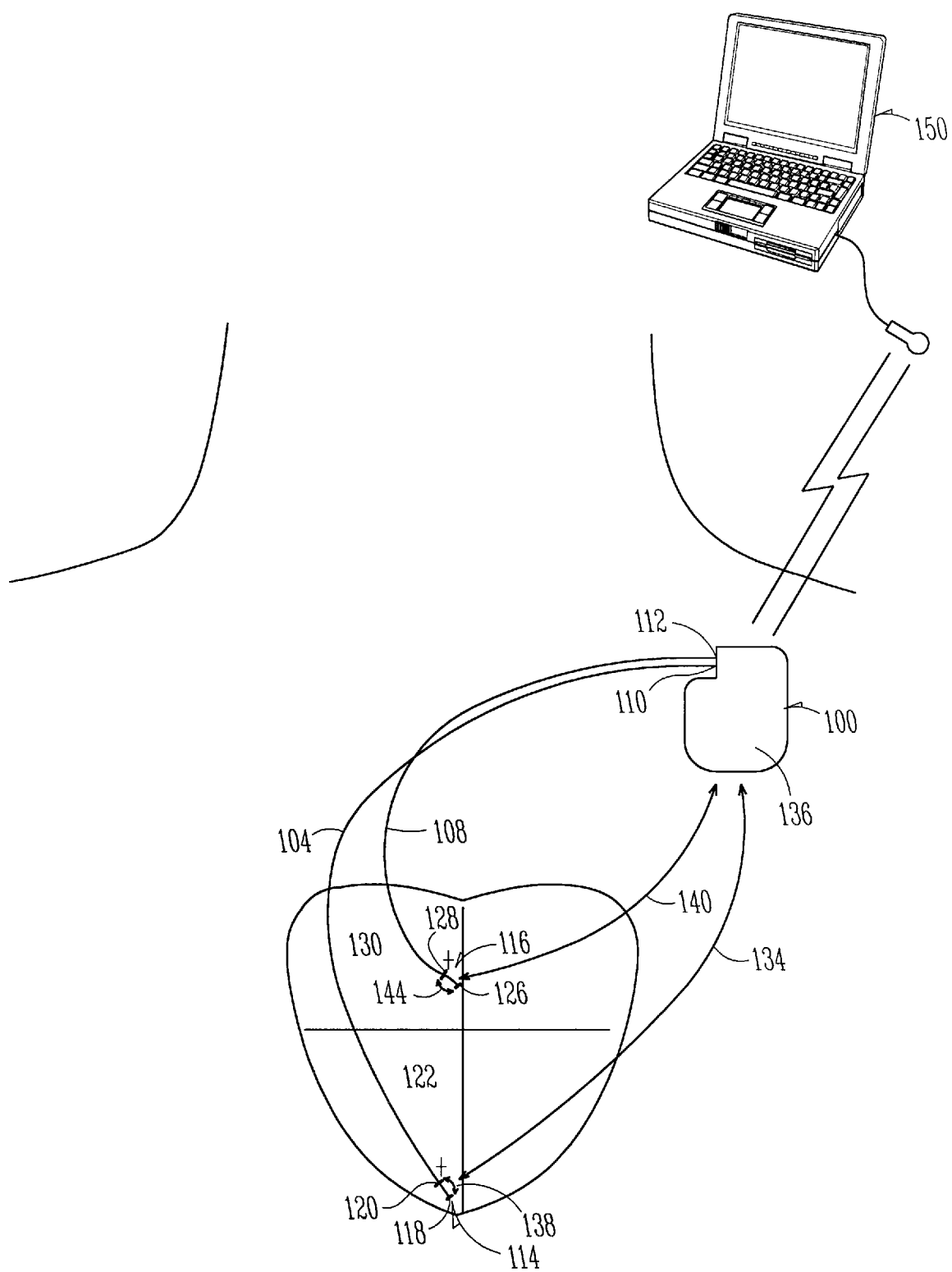
FIG. 1 is one embodiment of an apparatus according to the present subject matter that is implanted into a heart, from which segments have been removed to show detail.

FIG. 1 provides an illustration of unipolar and bipolar pacing and sensing vectors. In FIG. 1, there is shown an implantable pulse generator 100 coupled to a first cardiac lead 104 and a second cardiac lead 108. Each of the first cardiac lead 104 and the second cardiac lead 108 includes a proximal end (110 for the first lead 104 and 112 for the second lead 108) and a distal end (114 for the first lead 104 and 116 for the second lead 108). The first lead 104 further includes right ventricular electrodes that include a first right ventricular electrode 118 and a second right ventricular electrode 120. The first electrode 118 is shown positioned at the distal end 114 (at the tip of the lead) and the second electrode 120 is spaced proximal the first electrode 118 to allow for both electrodes to be positioned in the right ventricle 122. The second lead 108 further includes a first atrial sensing/pacing electrode 126 and a second atrial sensing/pacing electrode 128. The first electrode 126 is shown positioned at the distal end 116 (at the tip of the lead) and the second electrode 128 is spaced proximal the first electrode 126 to allow for both electrodes to be positioned in the right atrium 130. The cardiac leads 104 and 108 further include insulated conductors that extend between each of the electrodes and connectors at the proximal ends 110 and 112 of the first and second leads 104 and 108. The connectors allow each of the electrodes (118, 120, 126 and 128) to be coupled to electronic control circuitry within the implantable pulse generator 100.

The electronic control circuitry is used to sense cardiac signals and to deliver pacing pulses through the electrodes. A bipolar vector for a chamber is only available when a lead with at least two electrodes is implanted in, or near, a chamber of the heart. In FIG. 1, each of the first lead 104 and the second lead 108 are shown with at least two electrodes implanted within a chamber of the heart. With respect to the first lead 104, the electronic control circuitry is used to sense and/or pace either in a unipolar or a bipolar mode. Vector line 134 indicates either a unipolar pacing pulse or a unipolar cardiac signal between one of the first or second electrodes 118 or 120 and the housing 136 of the implantable medical device 100. In an alternative embodiment, vector line 138 indicates a bipolar pacing pulse or a bipolar cardiac signal sensed between the first and second electrodes 118 and 120 on the first lead 104.

With respect to the second lead 108, the electronic control circuitry is used to sense and/or pace either in a unipolar or a bipolar mode. Vector line 140 indicates either a unipolar pacing pulse or a unipolar cardiac signal between one of the first or second electrodes 126 or 128 and the housing 136 of the implantable medical device 100. In an alternative embodiment, vector line 144 indicates a bipolar pacing pulse or a bipolar cardiac signal sensed between the first and second electrodes 126 and 128 on the second lead 108. Different combinations of unipolar and bipolar sensing and pacing from each of the first lead 104 and the second lead 108 are programmed into the electronic control circuitry through the use of a medical device programmer 150.

In addition to the sensing and pacing vectors described above, it has been found that additional sensing and pacing vectors within and/or between cardiac chambers have benefits to providing treatment to a patient. In one embodiment, the present subject matter allows for additional sensing and/or pacing vectors between (e.g., left ventricular chamber and right ventricular chamber, left ventricular chamber and right atrial chamber, left atrial chamber and right atrial chamber) and within cardiac chambers when one or more cardiac leads are implanted in the left atrium and/or left ventricular region in addition to leads being implanted in the right ventricle and/or right atrium.

Figure 2:
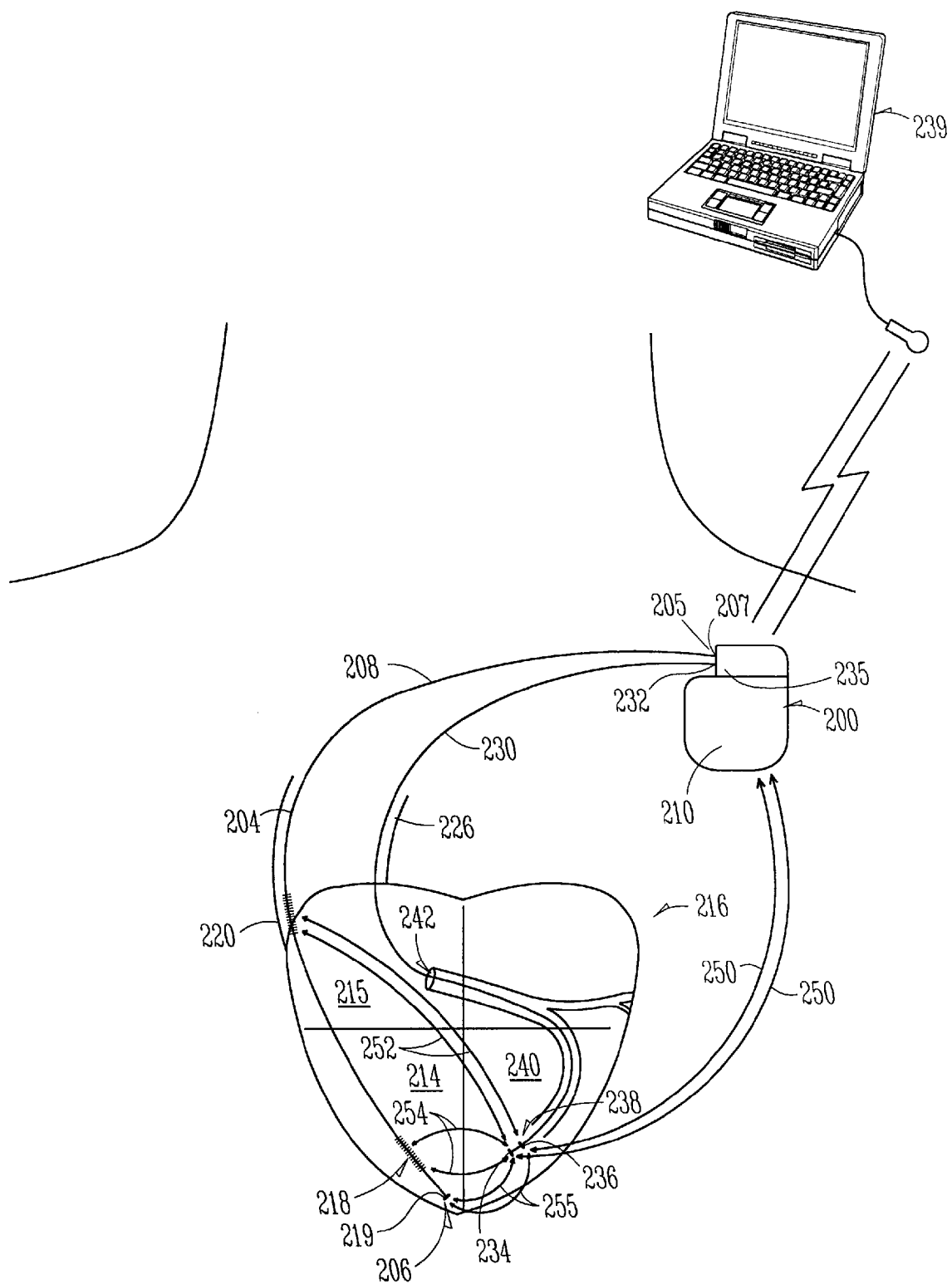
FIG. 2 is one embodiment of an apparatus according to the present subject matter that is implanted into a heart, from which segments have been removed to show detail.

FIG. 2 shows one embodiment of an apparatus 200 according to the present subject matter. In FIG. 2, the apparatus 200 includes a first lead 204 and a second lead 226. The first lead 204 has a proximal end 205 and a distal end 206 and includes a lead connector 207 having one or more connector terminals and a lead body 208. In one embodiment, examples of the lead connector 207 and connector terminals include, but are not limited to, LV-1, IS-1 UNI or IS-1 BI. Other lead connectors and connector terminals are possible. The lead 204 releasably attaches to an implantable pulse generator 210.

In one embodiment, the lead 204 is adapted to be inserted into and positioned within the right ventricle 214 and the right atrium 215 of the heart 216. The lead 204 includes right ventricular electrodes that include a first right ventricular electrode 218 and a second right ventricular electrode 219. In one embodiment, the first and second right ventricular electrodes 218 and 219 are adapted to be positioned in the right ventricular region 214. In an additional embodiment, the first right ventricular electrode 218 is a defibrillation coil electrode and the second right ventricular electrode 219 is a distal tip sensing/pacing electrode. In addition to the first and second right ventricular electrodes, the first lead 204 further includes additional electrodes, such as a first supraventricular electrode 220, where the first supraventricular electrode 220 is a defibrillation coil electrode.

One example of the first lead 204 is an endocardial lead sold under the trademark ENDOTAK (Cardiac Pacemaker, Inc./Guidant Corporation, St. Paul, Minn.), which is a tripolar, endocardial lead featuring a porous tip electrode. In one embodiment, the tip electrode 219 is placed in the apex of the right ventricle and serves as the cathode for intracardiac right ventricular electrogram rate sensing and pacing. Additionally, the two defibrillation coil electrodes serve as either an anode or a cathode for rate sensing and/or morphology sensing and for defibrillation. The present subject matter, however, uses the electrodes as either anodes or cathodes depending upon the programmed pacing and sensing vector direction.

The lead connector 207 electrically connects electrodes 218, 219 and 220 via conductors within the lead body 208 to the implantable pulse generator 210. The implantable pulse generator 210 contains control circuitry that receive cardiac signals sensed with the electrodes and generates pacing pulses to be delivered with the electrodes. The electronic control circuitry within the implantable pulse generator 210 also analyzes and detects certain types of arrhythmias and provides pacing pulses, cardioversion and/or defibrillation pulses to correct for them.

The apparatus 200 further includes a second lead 226, where the second lead 226 has a lead body 230 having a proximal end 232, a distal end 234 and includes a lead connector 235 having one or more connector terminals. In one embodiment, examples of the lead connector 235 and connector terminals include, but are not limited to, LV-1, IS-1 UNI or IS-1 BI. Other lead connectors and connector terminals are possible.

The second lead 226 further includes a first left ventricular electrode 236 and a second left ventricular electrode 238, where both the first and second left ventricular electrodes 236 and 238 are adapted to be positioned adjacent the left ventricle 240 via the coronary vasculature. In one embodiment, the first and second left ventricular electrodes 236 and 238 are pacing/sensing electrodes, where the first electrode 236 and the second electrode 238 are ring electrodes that either completely or partially encircles lead body 230. Alternatively, the second electrode 238 is a tip electrode positioned at the distal end 234 of the lead 226.

In one embodiment, the second lead 226 is adapted to be inserted through the coronary sinus vein 242 and through the great cardiac vein, or other coronary branch vein, to position the ventricular electrodes 236 and 238 adjacent the left ventricle 240 of the heart 216. In an alternative embodiment, the second lead 226 is an epicardial lead, where the electrodes on the lead 226 are positioned epicardially adjacent the left ventricle of the heart.

The lead 226 is releasably attached to the implantable pulse generator 210, where the connector terminals couple the ventricular electrodes 236 and 238 via lead conductors to the electronic control circuitry within the implantable pulse generator 210. The control circuitry within the implantable pulse generator 210 receives cardiac signals sensed through the use of the electrodes 236 and 238 and generates pacing pulses to be delivered through the use of the electrodes.

Sensing and pacing with electrodes 218, 219, 220, 236 and 238 and the housing of the implantable pulse generator 210 is a programmable feature of the control circuitry within the pulse generator 210. In one embodiment, programming the sensing and pacing vectors is accomplished through the use of a medical device programmer 239. The medical device programmer 239 is used to program specific pacing and sensing vectors that use one or both electrodes 236 and 238 in conjunction with different combinations of electrodes 218, 219, 220 and the housing of the implantable pulse generator 210.

In one embodiment, either of the ventricular electrodes 236 or 238 is used in unipolar sensing and pacing between the electrode (236 or 238) and the housing 210. Examples of these sensing and pacing vectors are shown generally at 250. In one example, the control circuitry of the pulse generator 210 is programmed to switch from unipolar sensing and pacing between one of the two electrodes 236 or 238 and the housing to unipolar sensing and pacing between the other electrode of 236 or 238 and the housing. In an additional embodiment, both ventricular electrodes 236 and 238 are used in unipolar sensing and pacing between the electrodes 236 and 238 and the housing 210. Alternatively, a bipolar sensing and pacing vector occurs between the two electrodes 236 and 238, where either 236 or 238 is the anode and the other electrode is the cathode.

In one embodiment, the electrodes 236 and 238 are used in sensing and pacing between the left and right ventricles of the heart. For example, one or both of the two electrodes 236 or 238 is used to sense cardiac signals and provide pacing pulses between the electrode(s) 236 and/or 238 and the first supraventricular electrode 220. In one embodiment, this pacing sensing vector is shown generally at 252. Alternatively, one or both of the two electrodes 236 and/or 238 is used to sense cardiac signals and provide pacing pulses between the electrode(s) 236 and/or 238 and the first right ventricular electrode 218. In one embodiment, this pacing sensing vector is shown generally at 254. In addition, one or both of the two electrodes 236 and/or 238 is used to sense cardiac signals and provide pacing pulses between the electrode(s) 236 and/or 238 and the second right ventricular electrode 219. In one embodiment, this pacing sensing vector is shown generally at 255. Pacing and sensing vectors 252, 254 and 255 are referred to herein as "extended" bipolar pacing/sensing vector, as the pacing and sensing occurs between implanted electrodes across a larger portion of the heart than is typical with a traditional bipolar pacing/sensing vector.

In one embodiment, electrodes 218, 219, 220, 236 and 238 are created from either platinum, platinum-iridium alloys or alloys which can include cobalt, iron, chromium, molybdenum, nickel and/or manganese. In addition, the second right ventricular electrode 219 and the second left ventricular electrode 238 are porous electrodes. Alternatively, the second right ventricular electrode 219, the first left ventricular electrode 236, and the second left ventricular electrode 238 are ring electrodes that either partially or fully encircle their respective lead bodies, 208 or 230, as previously discussed. In addition, the second right ventricular electrode 219 further includes a helical screw for positive fixation of the lead 204.

In one embodiment, the lead bodies 208 and 230 are formed of a biocompatible polymer such as silicone rubber and/or polyurethane. The lead bodies 208 and 230 further includes one or more lumens which are adapted to receive a stylet, or guidewire, for guiding and implanting the leads 204 and 226. In one embodiment, the lead bodies 208 and 230 include a lumen that extends from an opening at the proximal end of the lead to the distal end of the lead to allow the lead to be controlled through the use of the stylet, or guidewire. In one embodiment, the stylet lumen is formed from a lead conductor extending from the connector terminal and the proximal end of the lead, 204 and 226 to a distal most electrode on the lead (e.g., the second right ventricular electrode 219 and the second left ventricular electrode 238).

Figure 3:
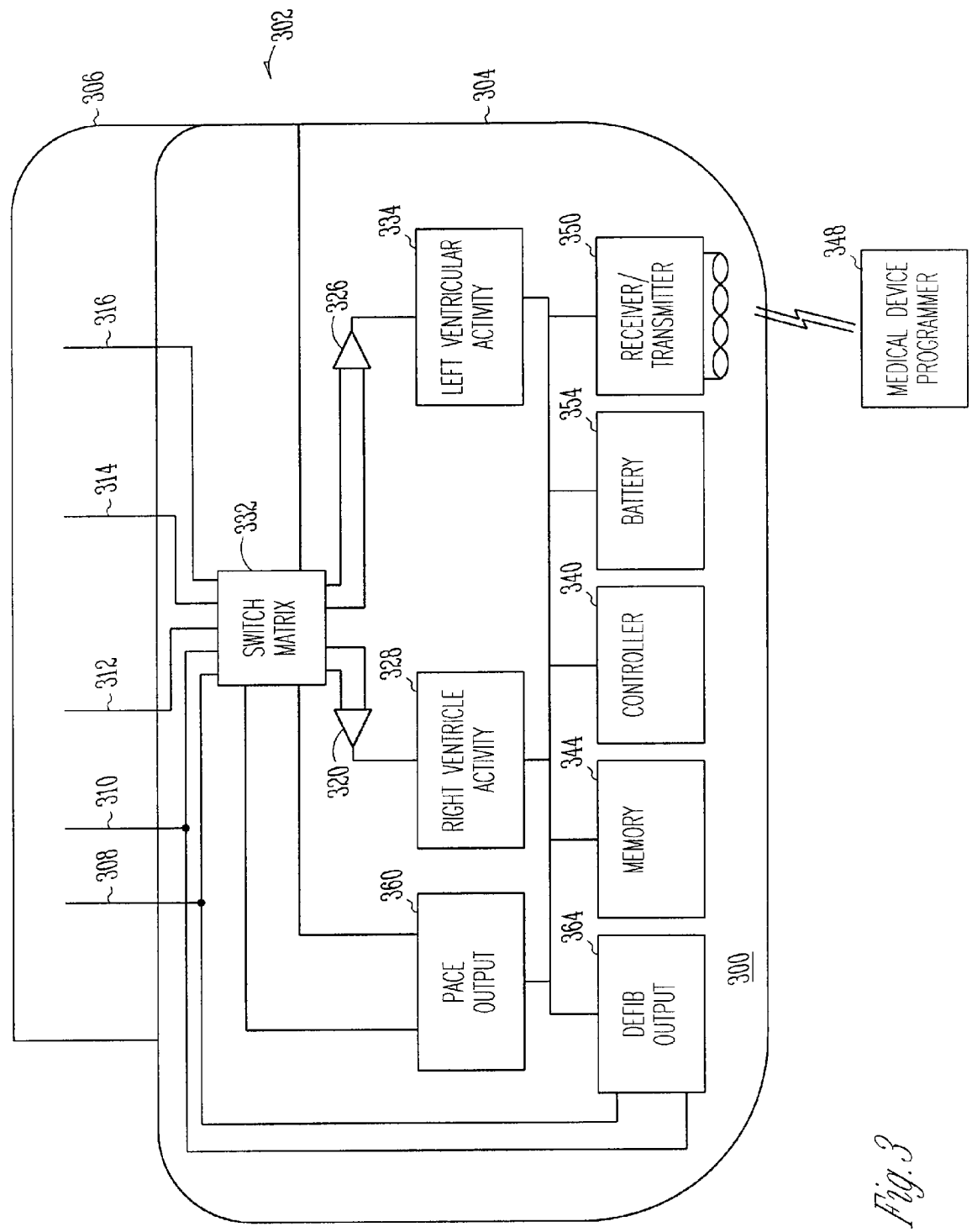
FIG. 3 is a block diagram of electronic control circuitry for one embodiment of an apparatus according to the present subject matter.

FIG. 3 shows one embodiment of control circuitry 300, as previously mentioned, for an implantable pulse generator 302. In the present embodiment, the implantable pulse generator 302 is adapted to receive the first and second leads (e.g., 204 and 226), as discussed.

The control circuitry 300 is contained within a hermetically sealed housing 304. The housing 304 is electrically conductive and acts as a reference electrode in unipolar pacing and sensing, as will be described below. The pulse generator 302 further includes a connector block 306 that receives the connector terminals of the cardiac leads, such as 204 and 226. The connector block 306 includes contacts 308, 310, 312, 314 and 316 that connect electrodes 220, 218, 219, 238 and 236, respectively, to sense amplifiers 320 and 326.

In one embodiment, an output from amp 320 is shown coupled to a right ventricular activity sensor 328 to allow for a bipolar cardiac signal to be sensed from the right ventricle 214 (FIG. 2) between the first right ventricular electrode 218 and the second right ventricular electrode 219 via switch matrix 332. In this embodiment, the extended bipolar cross chamber sensing is accomplished by the controller 340 configuring the switch matrix 332 such that the left ventricular activity sensor 334 receives an extended bipolar cardiac signal sensed between the second left ventricular electrode 238 and the first right ventricular electrode 218. Alternatively, the left ventricular activity sensor 334 receives the extended bipolar cardiac signal sensed between the first left ventricular electrode 236 and the first right ventricular electrode 218. The left ventricular activity sensor 334 also receives extended bipolar cardiac signal sensed between the second left ventricular electrode 238 and the first supraventricular electrode 220, in addition to an extended bipolar cardiac signal sensed between the first left ventricular electrode 236 and the first supraventricular electrode 220. In addition, the left ventricular activity sensor 334 receives the extended bipolar cardiac signal sensed between the first and second left ventricular electrodes 236 and 238 and the first right ventricular electrode 218. Alternatively, the left ventricular activity sensor 334 receives the extended bipolar cardiac signal sensed between the first and second left ventricular electrodes 236 and 238 and the second right ventricular electrode 219. Which combination of extended bipolar cardiac signals are sensed depends upon the sensing vectors programmed into the switch matrix 332 by control circuitry 300. FIG. 3 also shows the output from amp 326 coupled to a left ventricular activity sensor 334 to allow for a bipolar cardiac signal to be sensed from the left ventricle 240 (FIG. 2) between the first and second left ventricular electrodes 236 and 238.

The control circuitry 300 further includes a controller 340, where the controller 340 receives the cardiac signals from the sensing circuits 328 and 334 and analyzes the cardiac signals to determine when and if to deliver electrical energy pulses to the heart. In one embodiment, the controller 340 is a microprocessor, however, other circuitry under the control of software and/or firmware may be used as the controller 340.

In one embodiment, the controller 340 implements one or more analysis protocols stored in a memory 344 to analyze one or more of the sensed cardiac signals and to provide pacing, cardioversion and/or defibrillation therapy to one or more chambers of the heart under certain predetermined conditions. Memory 344 is also used to store one or more sensed cardiac signals to be downloaded to a medical device programmer 348 for analysis. In one embodiment, the control circuitry 300 communicates with the medical device programmer 348 through a receiver/transmitter 350, where cardiac signals, programs and operating parameters for the programs for the implantable medical device are transmitted and received through the use of the programmer 348 and the receiver/transmitter 350. Power for the control circuitry is supplied by a battery 354.

The controller 340 further controls a pace output circuit 360 and a defibrillation output circuit 364 to provide pacing, cardioversion and/or defibrillation therapy to one or more chambers of the heart under certain predetermined conditions. In one embodiment, the pace output circuit 360 is coupled to contacts 308, 310, 312, 314 and 316 via switch matrix 332 to allow for bipolar pacing between electrodes 218 and 219, and extended bipolar pacing between electrodes 236 and/or 238 and 218, 219 or 220, as previously described. In an additional, extended bipolar pacing and sensing occurs between electrodes 236 and 238, electrically coupled in common, and electrode 218, 219 or 220. In one embodiment, electrodes 236 and/or 238 are the cathode and electrodes 218, 219 and/or 220 are used as the anode in the extended bipolar pacing and sensing. Alternatively, electrodes 236 and/or 238 are the anode and electrodes 218, 219 and/or 220 are used as the cathode in the extended bipolar pacing and sensing. In an additional embodiment, when bipolar pacing occurs between electrodes 218 and 219, electrode 218 is the cathode and electrode 219 is the anode.

In addition to the extended bipolar sensing and pacing, electrode 236 and/or 238 are used in conjunction with the conductive housing 304 of the implantable pulse generator to allow for unipolar sensing and pacing between either of electrodes 236 or 238 and the housing 304. In an additional embodiment, the described polarity of the electrodes used in the bipolar pacing and sensing is reversed to allow for additional options in providing therapy to a patient.

The different combinations of the pacing and sensing vectors are programmable features that are selected and implemented in the implantable pulse generator 302 through the use of the medical device programmer 348. Thus, different combinations of pacing and sensing vectors (as described above) are selected and programmed based on each patient's specific needs. In addition, the programmable nature of the sensing and pacing vectors described herein allows for one or more of the sensing and/or pacing vectors to be altered based on sensed cardiac signals and the response to the pacing pulses delivered to the patient's heart.

Figure 4:
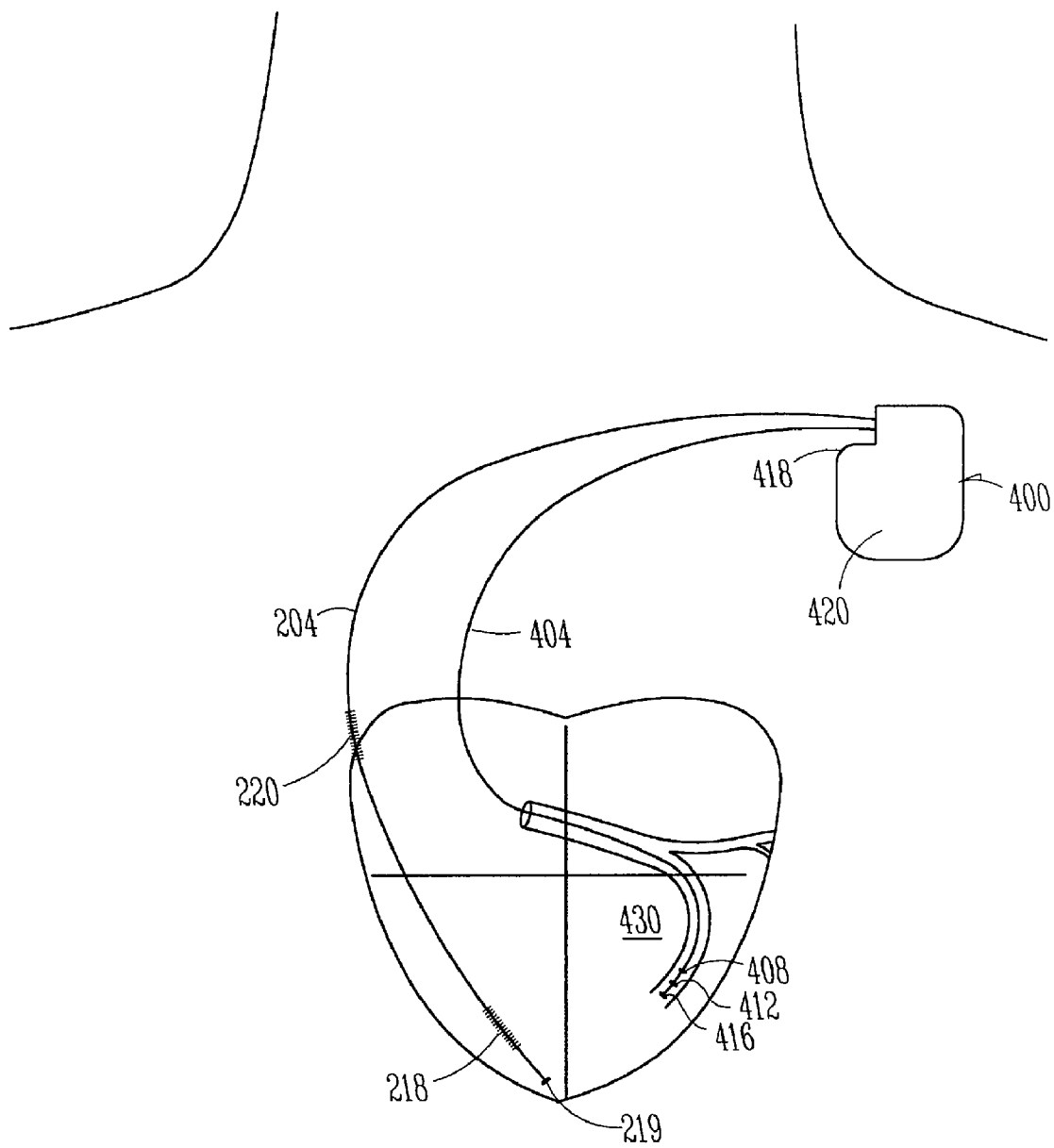
FIG. 4 is one embodiment of an apparatus according to the present subject matter that is implanted into a heart, from which segments have been removed to show detail.

FIG. 4 shows an additional embodiment of an apparatus 400 according to the present subject matter. In FIG. 4, the apparatus 400 includes a first lead 204, as described above for FIG. 2. FIG. 4 further includes a second lead 404, where the second lead 404 includes a plurality of electrodes. In one embodiment, the second lead 404 includes a first left ventricular electrode 408, a second left ventricular electrode 412 and a third left ventricular electrode 416.

Lead 404 includes a lead connector 418 having connector terminals for 20 coupling the electrodes 408, 412 and 416 via conductors within the lead body to the control circuitry within the implantable pulse generator 420. In one embodiment, the electrodes 408, 412 and 416 are adapted to be positioned adjacent the left ventricle 430 via the coronary vasculature. In one embodiment, the first, second and third left ventricular electrodes 408, 412 and 416 are pacing/sensing electrodes, where the electrodes are all ring electrodes that either completely or partially encircles lead body, or are a combination of ring electrodes and distal tip electrode positioned at the distal end of the lead 404. In addition, the lead body of the lead 404 forms a helix that is adapted to allow for the electrodes 408, 412 and 416 to better contact the cardiac tissue adjacent the left ventricle of the heart.

In one embodiment, the first and second left ventricular electrodes 408 and 412 are electrically connected in common, where pacing and sensing signals occur between combinations of the first and second left ventricular electrodes 408 and 412, in common, and the third left ventricular electrode 416. In an alternative embodiment, the first and second left ventricular electrodes 408 and 412 both have the same electrical polarity (e.g., anode or cathode), but are not electrically coupled in common. Thus, each electrode 408 and 412 is electrically isolated, but has the same electrical polarity. The control circuitry within the implantable pulse generator 420 then controls each electrode for delivering pacing signals and sensing cardiac signals to the heart. In one embodiment, this allows the control circuitry to individually adjust the output of one or both the electrodes 408 and 412 based on the pacing threshold of the patient.

In an additional embodiment, the control circuitry is programmable to select and switch between sensing unipolar cardiac signal and/or delivering unipolar pacing pulses between each electrodes 408, 412 or 416 and the housing of the implantable pulse generator 420. Additionally, the control circuitry is also programmable to select and switch between sensing extended bipolar signals and/or delivering extended bipolar pacing pulses between each electrodes 408, 412 or 416 and either the first right ventricular electrode 218, the second right ventricular electrode 219 or the first supraventricular electrode 220.

Figure 5:
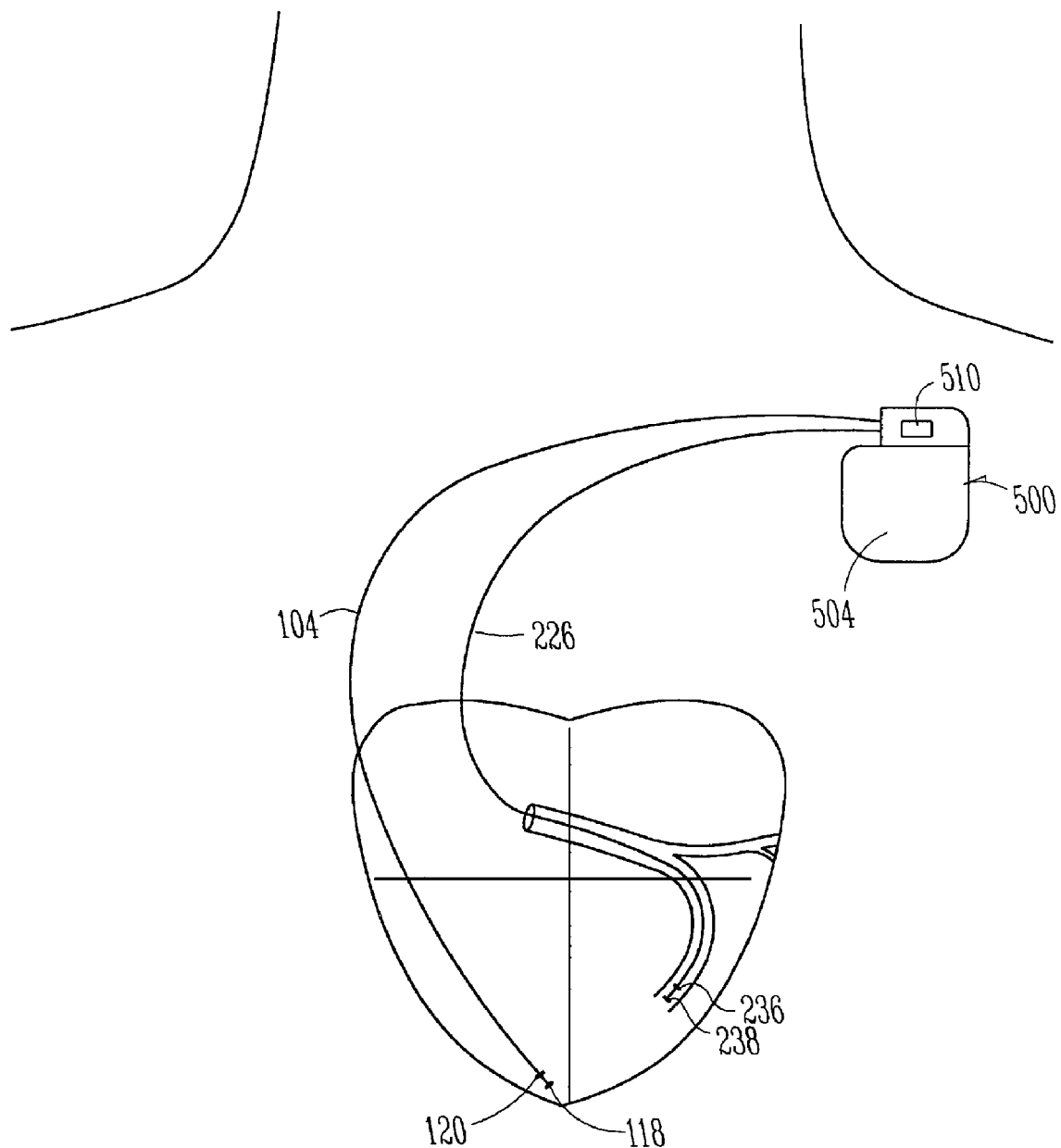
FIG. 5 is one embodiment of an apparatus according to the present subject matter that is implanted into a heart, from which segments have been removed to show detail.

FIG. 5 shows an additional embodiment of an apparatus 500 according to the present subject matter. In FIG. 5, the apparatus 500 includes the first lead 104, as described above for FIG. 1, and lead 226, as described above for FIG. 2. This embodiment allows for combinations of electrodes 118, 120 of the first lead 104 and electrodes 236 and 238 of the second lead 226 to be programmed to sense cardiac signals and/or deliver pacing pulses between any number of electrode combinations. For example, extended bipolar cardiac signals are sensed between and/or pacing pulses are delivered between electrode 236 and electrode 118 and/or 120, and/or extended bipolar cardiac signals are sensed between and/or pacing pulses are delivered between electrode 238 and electrode 118 and/or 120. The control circuitry of the implantable pulse generator 504 is programmable to select and switch between sensing unipolar cardiac signal and/or delivering unipolar pacing pulses between each electrodes 118, 120, 236 or 238 and the housing of the implantable pulse generator 504. Additionally, the control circuitry is also programmable to select and switch between sensing unipolar cardiac signal and/or delivering unipolar pacing pulses between each electrodes 236 and 238 and either electrode 118 or 120.

In an additional embodiment, the connector blocks of any of the implantable pulse generators described above can further include a reference electrode for use in sensing unipolar cardiac signals and delivering unipolar pacing pulses between any of the aforementioned electrodes (e.g., 118, 120, 218, 219, 220, 236, 238, 408, 412 or 416). An example of the connector block electrode is shown in FIG. 5 at 510.

Figure 6:
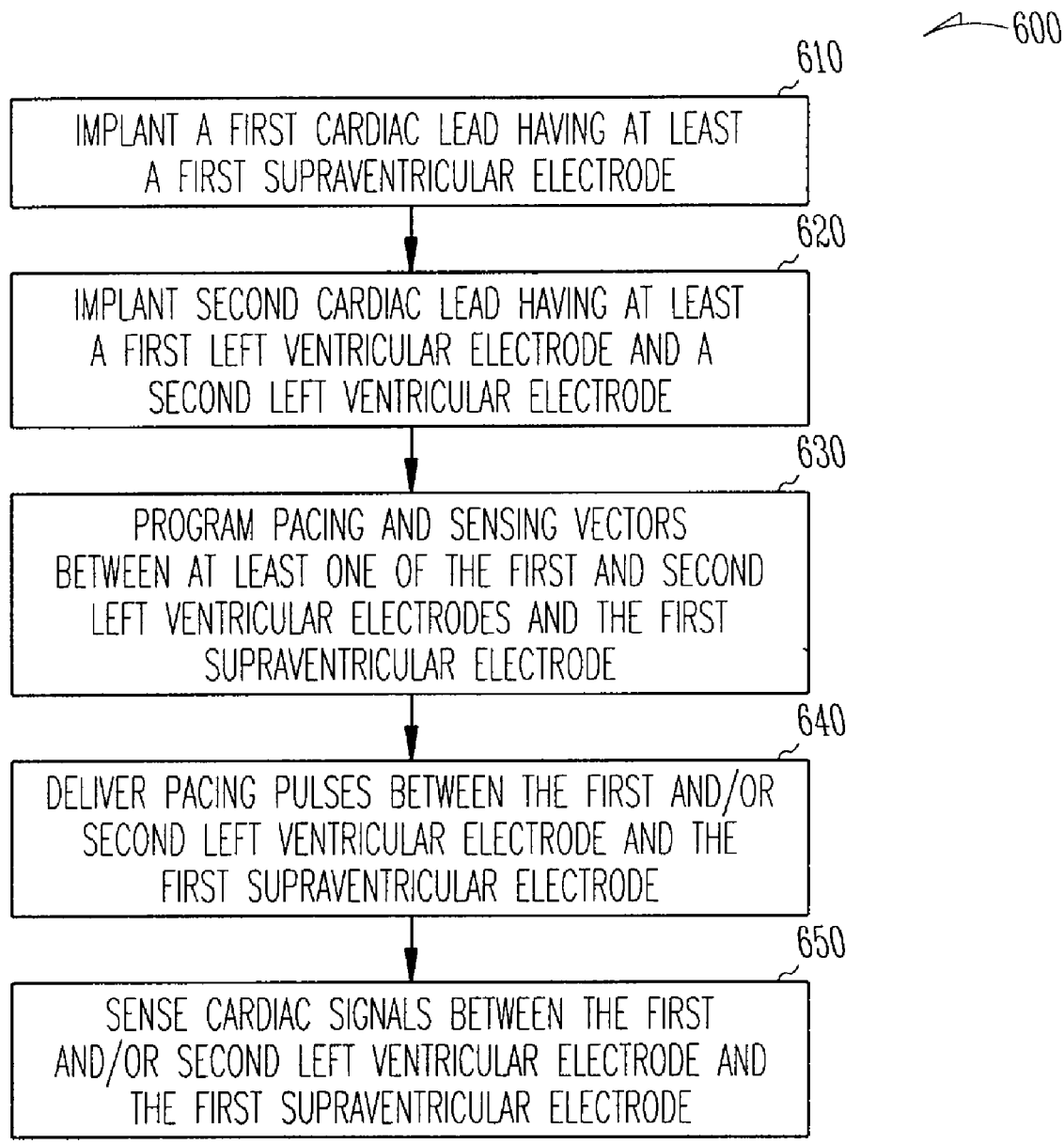
FIG. 6 is a flow chart of a method according to one embodiment of the present subject matter.

FIG. 6 shows one embodiment of a method 600 according to one aspect of the present subject matter. At 610, a first cardiac lead having at least a first supraventricular electrode is implanted within a heart. In one embodiment, the first supraventricular electrode is positioned within the right atrium of the heart and/or a major vein leading to the right atrium. At 620, a second cardiac lead having at least a first left ventricular electrode and a second left ventricular electrode is implanted within a heart. In one embodiment, the first and second left ventricular electrodes are positioned in a left ventricular region of the heart.

Specific examples of the first supraventricular electrode and the first and second left ventricular electrodes were presented above. These examples, however, are not intended to be limiting and different examples of the first supraventricular electrode and the first and second left ventricular electrodes are possible. These additional examples include, but are not limited to, the first supraventricular electrode taking the form of a pacing/sensing electrode, such as a ring electrode. Additionally, one or both of the left ventricular electrodes can take the form of a coil electrode that can be used in conjunction with any of the aforementioned structures for the first supraventricular or ventricular electrodes.

At 630, pacing pulse vectors and sensing vectors are programmed between one or more of the first left ventricular electrode and the second left ventricular electrode, and the first supraventricular electrode in the right atrial region. At 640, pacing pulses are delivered between the first and/or second left ventricular electrode in the left ventricular region and the first supraventricular electrode in the right atrial region, according to the programmed pacing pulse vectors. In one embodiment, the first and/or second left ventricular electrode is used as the cathode, while the first supraventricular electrode is used as the anode. In an alternative embodiment, the first supraventricular electrode is used as the cathode, while the first and/or the second left ventricular electrode is used as the anode.

In addition to providing pacing pulses between the first and/or second left ventricular electrode and the first supraventricular electrode, sensing vectors between the first left ventricular electrode and/or the second left ventricular electrode, and the first supraventricular electrode are sensed at 650 according to the programmed sensing vector. In one embodiment, the cardiac signal is sensed where the first and/or second left ventricular electrode is an anode and the first supraventricular electrode is a cathode. In an alternative embodiment, the cardiac signal is sensed where the first supraventricular electrode is an anode and the first and/or second left ventricular electrode is a cathode. In an additional embodiment, the housing of an implantable pulse generator is conductive and is used in an electrode in common with the first supraventricular electrode, as previously discussed.

Figure 7:
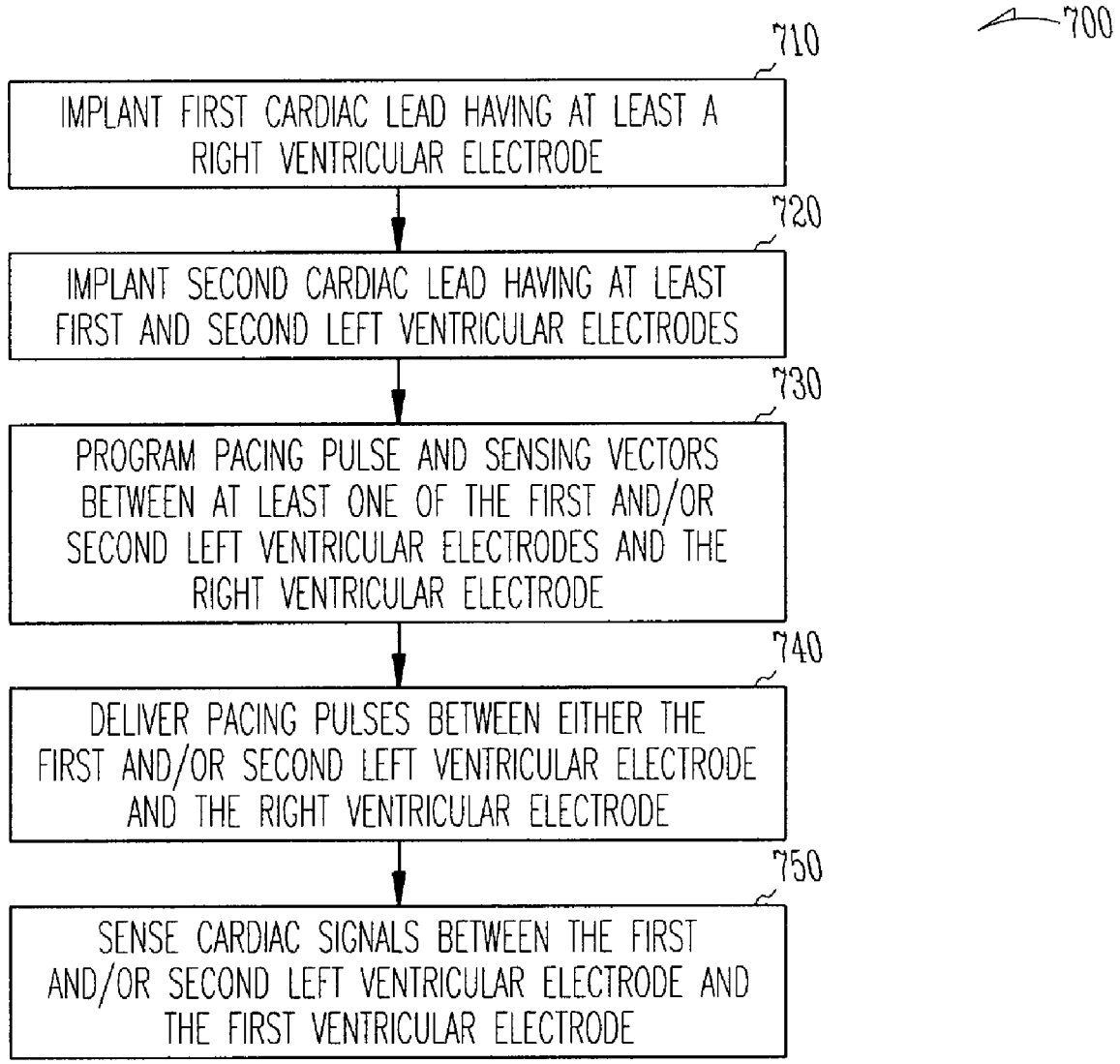
FIG. 7 is a flow chart of a method according to one embodiment of the present subject matter.

FIG. 7 shows one embodiment of a method 700 according to one aspect of the present subject matter. At 710, a first cardiac lead having at least a right ventricular electrode is implanted within a heart. In one embodiment, the right ventricular electrode is either a defibrillation electrode, such as the first right ventricular electrode 218, or a pace/sense electrode, such as the second right ventricular electrode 219. These examples, however, are not intended to be limiting and different examples of the right ventricular electrode are possible. In one embodiment, the right ventricular electrode is positioned within the right ventricle of the heart.

At 720, a second cardiac lead having at least a first left ventricular electrode and a second left ventricular electrode is implanted within a heart. In one embodiment, the first and second left ventricular electrodes are positioned in a left ventricular region of the heart. In one embodiment, the first and second left ventricular electrodes are as previously described. These examples, however, are not intended to be limiting and different examples of the first and second left ventricular electrodes are possible. For example, one or both of the left ventricular electrodes can take the form of a coil electrode that can be used in conjunction with any of the aforementioned structures for the supraventricular or ventricular electrodes.

At 730, pacing pulse vectors and sensing vectors are programmed between one or more of the first and second left ventricular electrodes, and the right ventricular electrode. At 740, pacing pulses are delivered between the first and/or second left ventricular electrode and the right ventricular electrode, according to the programmed pacing pulse vectors. In one embodiment, the first and/or second left ventricular electrode is used as the cathode, while the right ventricular electrode is used as the anode. In an alternative embodiment, the right ventricular electrode is used as the cathode, while the first and/or the second left ventricular electrode is used as the anode.

In addition to providing pacing pulses between the first and/or second left ventricular electrode and the right ventricular electrode, sensing vectors between one, or both, of the first and second left ventricular electrodes and the right ventricular electrode are sensed at 750 according to the programmed sensing vector. In one embodiment, the cardiac signal is sensed where the first and/or second left ventricular electrode is an anode and the right ventricular electrode is a cathode. In an alternative embodiment, the cardiac signal is sensed where the right ventricular electrode is an anode and the first and/or second left ventricular electrode is a cathode. In an additional embodiment, the housing of an implantable pulse generator is conductive and is used in an electrode in common with the right ventricular electrode, as previously discussed.

Figure 8:
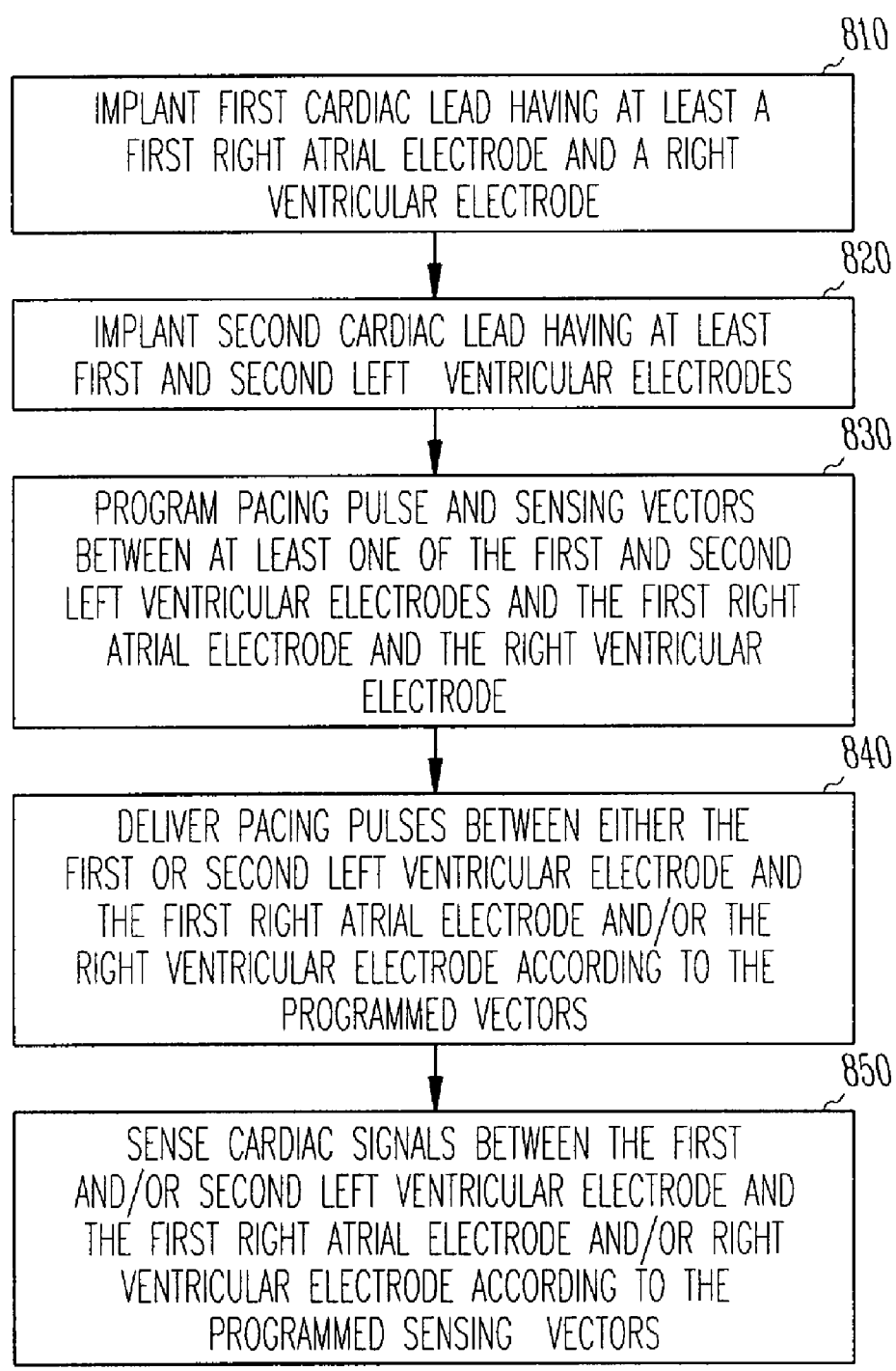
FIG. 8 is a flow chart of a method according to one embodiment of the present subject matter.

FIG. 8 shows one embodiment of a method 800 according to one aspect of the present subject matter. At 810, a first cardiac lead having at least a first supraventricular electrode and a first ventricular electrode is implanted within a heart. In one embodiment, the first supraventricular electrode is positioned within the right atrium of the heart, while the first ventricular electrode is positioned within the right ventricle of the heart. In one embodiment, the right ventricular electrode is either a defibrillation electrode, such as the first right ventricular electrode 218, or a pace/sense electrode, such as the second right ventricular electrode 219. These examples, however, are not intended to be limiting and different examples of the right ventricular electrode are possible. At 820, a second cardiac lead having at least a first left ventricular electrode and a second left ventricular electrode is implanted within a heart. In one embodiment, the first and second left ventricular electrodes are positioned in a left ventricular region of the heart.

Specific examples of the first supraventricular and ventricular electrodes and the first and second left ventricular electrodes were presented above. These examples, however, are not intended to be limiting and different examples of the first supraventricular and ventricular electrodes and the first and second left ventricular electrodes are possible. These additional examples include, but are not limited to, the first supraventricular or ventricular electrode taking the form of a pacing/sensing electrode, such as a ring electrode. Additionally, one or both of the left ventricular electrodes can take the form of a coil electrode that can be used in conjunction with any of the aforementioned structures for the first supraventricular or ventricular electrodes.

At 830, pacing pulse vectors and sensing vectors are programmed between one or more of the first left ventricular electrode and/or the second left ventricular electrode, and the first supraventricular electrode in the right atrial region and the right ventricular electrode in the right ventricle. At 840, pacing pulses are delivered between either the first and/or second left ventricular electrode and the first supraventricular electrode and/or the first right ventricular electrode, according to the programmed pacing pulse vectors. In one embodiment, the first and/or second left ventricular electrode is used as the cathode, while the first supraventricular and/or the right ventricular electrode is used as the anode. In an alternative embodiment, the first supraventricular and/or right ventricular electrode is used as the cathode, while the first and/or the second left ventricular electrode is used as the anode.

In addition to providing pacing pulses between the first and/or second left ventricular electrode and the first supraventricular electrode and/or right ventricular electrode, sensing vectors between one or both of the first and/or second left ventricular electrodes, and the first supraventricular and/or the right ventricular electrode are sensed at 850 according to the programmed sensing vector. In one embodiment, the cardiac signal is sensed where the first and/or second left ventricular electrode is an anode and the first supraventricular electrode and/or the right ventricular electrode is a cathode. In an alternative embodiment, the cardiac signal is sensed where the first supraventricular electrode and/or the right ventricular electrode is an anode and the first and/or second left ventricular electrode is a cathode. In an additional embodiment, the housing of an implantable pulse generator is electrically conductive and used as an electrode in common with the first supraventricular electrode and/or the right ventricular electrode, as previously discussed.

Figure 9:
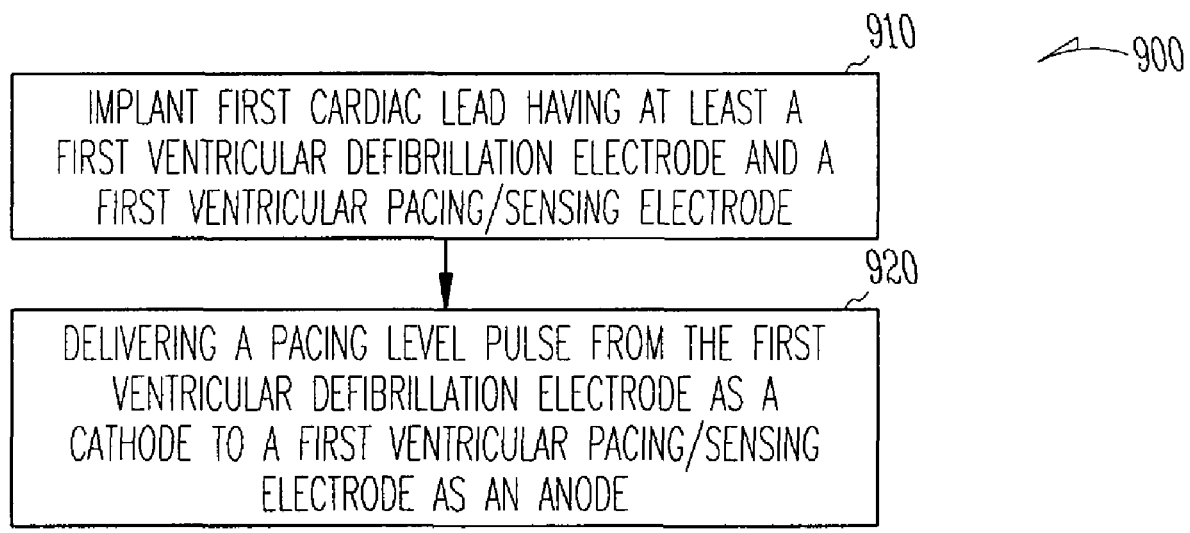
FIG. 9 is a flow chart of a method according to one embodiment of the present subject matter.

FIG. 9 shows one embodiment of a method 900 according to an additional aspect of the present subject matter. At 910, a first cardiac lead having at least a first right ventricular electrode and a second right ventricular electrode is implanted within a heart. In one embodiment, the first and second right ventricular electrodes are positioned within the right ventricle of the heart. Specific examples of the first and second right ventricular electrodes were presented above, where the first right ventricular electrode is a defibrillation coil electrode positioned in a right ventricular region, and the second right ventricular electrode is a pacing/sensing electrode located at or near the distal tip of the lead and positioned in an apex of the right ventricular region. At 920, a pacing level pulse is delivered from a first ventricular defibrillation electrode as a cathode to a first ventricular pacing/sensing electrode as an anode.

Figure 10:
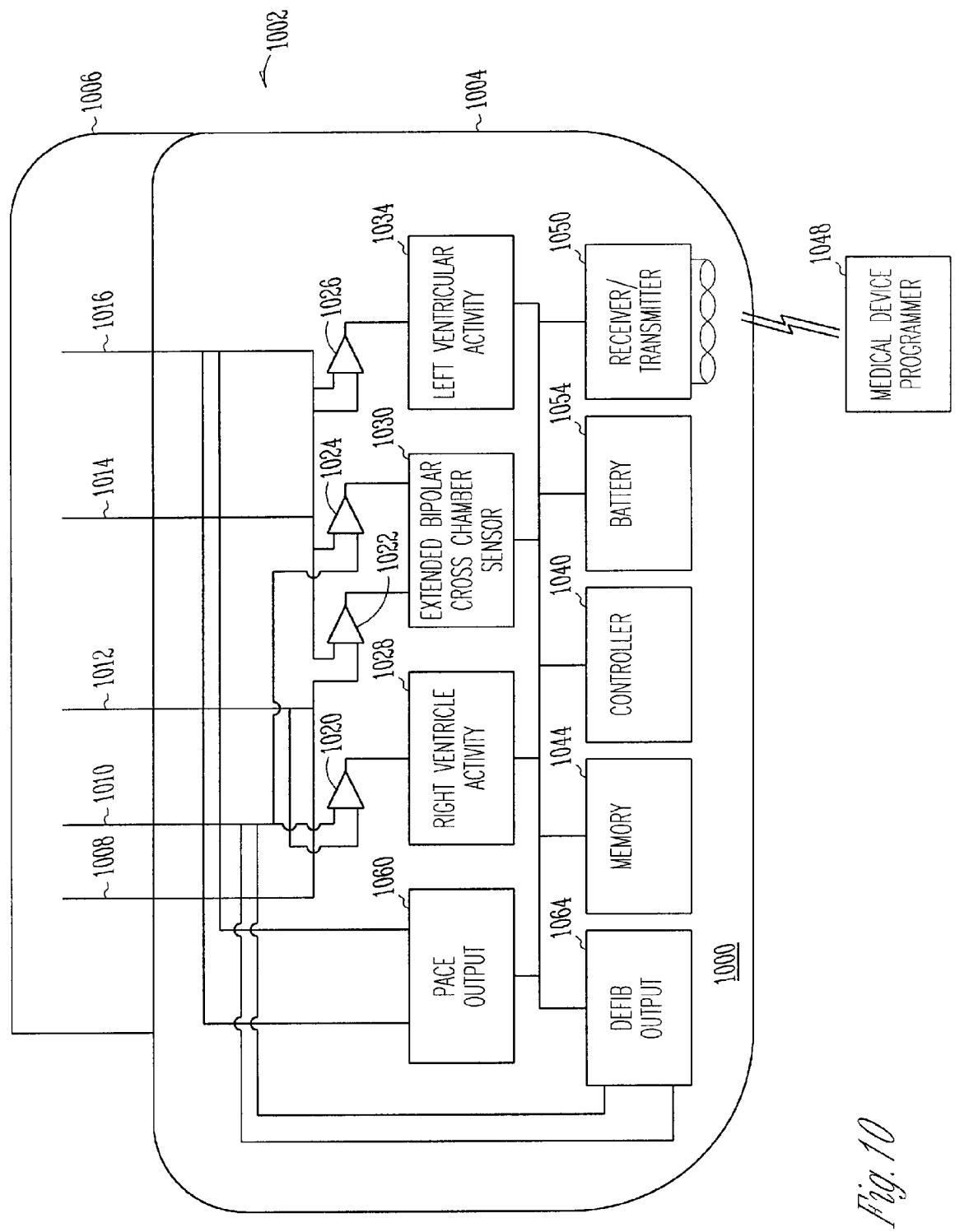
FIG. 10 is a block diagram of electronic control circuitry for one embodiment of an apparatus according to the present subject matter.

FIG. 10 shows an additional embodiment of control circuitry 1000, as previously mentioned, for an implantable pulse generator 1002. In the present embodiment, the implantable pulse generator 1002 is adapted to receive the first and second leads (e.g., 204 and 226, 204 and 404, 104 and 226), as previously discussed.

The control circuitry 1000 is contained within a hermetically sealed housing 1004. The housing 1004 is electrically conductive and acts as a reference electrode in unipolar pacing and sensing, as will be described below. The pulse generator 1002 further includes a connector block 1006 that receives the connector terminals of the cardiac leads, such as 204 and 226, 204 and 404, or 104 and 226. In one embodiment, the connector block 1006 includes contacts 1008, 1010, 1012, 1014 and 1016 that connect electrodes 220, 218, 219, 238 and 236, respectively, to sense amplifiers 1020, 1022, 1024 and 1026.

In one embodiment, an output from amp 1020 is shown coupled to a right ventricular activity sensor 1028 to allow for a bipolar cardiac signal to be sensed from the right ventricle 214 (FIG. 2) between the first right ventricular electrode 218 and the second right ventricular electrode 219. In addition, an output from amps 1022 and 1024 is shown coupled to an extended bipolar cross chamber sensor 1030. In this embodiment, the extended bipolar cross chamber sensor 1030 receives an extended bipolar cardiac signal sensed between the second left ventricular electrode 238 and the first right ventricular electrode 218. Alternatively, the extended bipolar cross chamber sensor 1030 receives the extended bipolar cardiac signal sensed between the first left ventricular electrode 236 and the first right ventricular electrode 218. The extended bipolar cross chamber sensor 1030 also receives extended bipolar cardiac signal sensed between the second left ventricular electrode 238 and the first supraventricular electrode 220, in addition to an extended bipolar cardiac signal sensed between the first left ventricular electrode 236 and the first supraventricular electrode 220. In addition, the extended bipolar cross chamber sensor 1030 receives the extended bipolar cardiac signal sensed between the first and second left ventricular electrodes 236 and 238 and the first right ventricular electrode 218. Alternatively, the extended bipolar cross chamber sensor 1030 receives the extended bipolar cardiac signal sensed between the first and second left ventricular electrodes 236 and 238 and the second right ventricular electrode 219. Which combination of extended bipolar cardiac signals are sensed depends upon the sensing vectors programmed into the control circuitry 1000. FIG. 10 also shows an output from amp 1026 coupled to a left ventricular activity sensor 1034 to allow for a bipolar cardiac signal to be sensed from the left ventricle 240 (FIG. 2) between the first and second left ventricular electrodes 236 and 238.

The control circuitry 1000 further includes a controller 1040, where the controller 1040 receives the cardiac signals from the sensing circuits 1028, 1030 and 1034 and analyzes the cardiac signals to determine when and if to deliver electrical energy pulses to the heart. In one embodiment, the controller 1040 is a microprocessor, however, other circuitry under the control of software and/or firmware may be used as the controller 1040.

In one embodiment, the controller 1040 implements one or more analysis protocols stored in a memory 1044 to analyze one or more of the sensed cardiac signals and to provide pacing, cardioversion and/or defibrillation therapy to one or more chambers of the heart under certain predetermined conditions. Memory 1044 is also used to store one or more sensed cardiac signals to be downloaded to a medical device programmer 1048 for analysis. In one embodiment, the control circuitry 1000 communicates with the medical device programmer 1048 through a receiver/transmitter 1050, where cardiac signals, programs and operating parameters for the programs for the implantable medical device are transmitted and received through the use of the programmer 1048 and the receiver/transmitter 1050. Power for the control circuitry is supplied by a battery 1054.

The controller 1040 further controls a pace output circuit 1060 and a defibrillation output circuit 1064 to provide pacing, cardioversion and/or defibrillation therapy to one or more chambers of the heart under certain predetermined conditions. In one embodiment, the pace output circuit 1060 is coupled to contacts 1008, 1010, 1012, 1014 and 1016 to allow for bipolar pacing between electrodes 218 and 219, and extended bipolar pacing between electrodes 236 and/or 238 and 218, 219 or 220, as previously described. In an additional, extended bipolar pacing and sensing occurs between electrodes 236 and 238, electrically coupled in common, and electrode 218, 219 or 220. In one embodiment, electrodes 236 and/or 238 are the cathode and electrodes 218, 219 and/or 220 are used as the anode in the extended bipolar pacing and sensing. Alternatively, electrodes 236 and/or 238 are the anode and electrodes 218, 219 and/or 220 are used as the cathode in the extended bipolar pacing and sensing. In an additional embodiment, when bipolar pacing occurs between electrodes 218 and 219, electrode 218 is the cathode and electrode 219 is the anode.

In addition to the extended bipolar sensing and pacing, electrode 236 and/or 238 are used in conjunction with the conductive housing 1004 of the implantable pulse generator to allow for unipolar sensing and pacing between either of electrodes 236 or 238 and the housing 1004. In an additional embodiment, the described polarity of the electrodes used in the bipolar pacing and sensing is reversed to allow for additional options in providing therapy to a patient.

The different combinations of the pacing and sensing vectors are programmable features that are selected and implemented in the implantable pulse generator 1002 through the use of the medical device programmer 1048. Thus, different combinations of pacing and sensing vectors (as described above) are selected and programmed based on each patient's specific needs. In addition, the programmable nature of the sensing and pacing vectors described herein allows for one or more of the sensing and/or pacing vectors to be altered based on sensed cardiac signals and the response to the pacing pulses delivered to the patient's heart.

In addition to the apparatus and methods described for providing pacing and sensing across ventricular regions of the heart, the present subject matter can also be used in a system having electrodes implanted in and around the supraventricular region of the heart. So, the present subject matter could be used to sense and pace bipolarly across the right and left atrium of the heart.

In addition to the apparatus and methods for providing pacing and sensing across the regions of the heart using two left ventricular electrodes, the present subject matter can also use a cardiac lead having a plurality of left ventricular electrodes, such as those shown and described in the example of FIG. 4.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A method, comprising:
programming at least one extended pacing pulse vector between a first supraventricular electrode in a right atrial region and at least one of a first left ventricular electrode and a second left ventricular electrode in a left ventricular region; and
delivering a pacing pulse according to the programmed extended pacing pulse vector between the first supraventricular electrode and at least one of the first left ventricular electrode and the second left ventricular electrode.

2. The method of claim 1, wherein programming at least one extended pacing vector includes programming a first supraventricular electrode in a right atrial region and a commonly connected first left ventricular electrode and second left ventricular electrode.

3. The method of claim 1, wherein programming at least one extended pacing vector includes programming at least one extended pacing vector between the first supraventricular electrode in a right atrial region and at least one of the first left ventricular electrode, the second left ventricular electrode, and a third left ventricular electrode in a left ventricular region, and wherein delivering a pacing pulse includes delivering a pacing pulse according to the programmed extended pacing pulse vector between the first supraventricular electrode and combinations of the first, second, and third left ventricular electrodes.

4. The method of claim 3, further including:
programming a second extended pacing vector including a housing of an implantable pulse generator and at least one of the first left ventricular electrode, the second left ventricular electrode, and a third left ventricular electrode in the left ventricular region; and
delivering a pacing pulse according to the programmed second extended pacing pulse vector.

5. The method of claim 3, further including:
programming a second extended pacing vector including first supraventricular electrode in a right atrial region and a housing of an implantable pulse generator; and
delivering a pacing pulse according to the programmed second extended pacing pulse vector.

6. The method of claim 3, further including:
programming a second extended pacing vector including a connector block electrode of an implantable pulse generator and at least one of the first left ventricular electrode, the second left ventricular electrode, and a third left ventricular electrode in a left ventricular region; and
delivering a pacing pulse according to the programmed second extended pacing pulse vector.

7. The method of claim 3, further including:
programming a second extended pacing vector including first supraventricular electrode in a right atrial region and a connector block electrode of an implantable pulse generator; and
delivering a pacing pulse according to the programmed second extended pacing pulse vector.

8. A method, comprising:
programming at least one extended sensing vector between a first supraventricular electrode in a right atrial region and at least one of a first left ventricular electrode and a second left ventricular electrode in a left ventricular region; and
sensing a cardiac signal between the first supraventricular electrode and at least one of the first left ventricular electrode and the second left ventricular electrode according to the programmed extended sensing vector.

9. The method of claim 8, further including:
programming at least one extended sensing vector between a right ventricular electrode in a right ventricular region and at least one of a first left ventricular electrode and a second left ventricular electrode in a left ventricular region; and
sensing a cardiac signal between the right ventricular electrode and at least one of the first left ventricular electrode and the second left ventricular electrode according to the programmed extended sensing vector.

10. The method of claim 8, further including programming at least one second extended sensing vector between the first supraventricular electrode in a right atrial region and a connector block electrode of an implantable pulse generator; and
sensing a cardiac signal between the first supraventricular electrode in a right atrial region and connector block electrode of an implantable pulse generator according to the programmed second extended sensing vector.

11. A method, comprising:
programming at least one first extended pacing pulse vector between (1) at least one of a first left ventricular electrode and a second left ventricular electrode in a left ventricular region, and (2) a first supraventricular electrode in a right atrial region;
delivering a pacing pulse according to the first programmed extended pacing pulse vector; and
programming at least one second extended pacing pulse vector between (1) at least one of the first left ventricular electrode and the second left ventricular electrode and (2) a connector block electrode of an implantable pulse generator, and wherein delivering the pacing pulse includes delivering the pacing pulse according to the second programmed extended pacing pulse vector.

12. A method, comprising:
programming at least one first extended pacing pulse vector between (1) at least one of a first left ventricular electrode and a second left ventricular electrode in a left ventricular region, and (2) a first supraventricular electrode in a right atrial region commonly connected to a connector block electrode of an implantable pulse generator;
delivering a pacing pulse according to the first programmed extended pacing pulse vector; and
programming at least one second extended pacing pulse vector between (1) at least one of the first left ventricular electrode and the second left ventricular electrode and (2) a first right ventricular electrode in a right ventricular region, and wherein delivering a pacing pulse includes delivering a pacing pulse according to the second programmed extended pacing pulse vector.

13. A method, comprising:
programming at least one first extended pacing pulse vector between (1) at least one of a first left ventricular electrode and a second left ventricular electrode in a left ventricular region, and (2) a right ventricular electrode in a right ventricular region;
delivering a pacing pulse according to the programmed first extended pacing pulse vector; and
programming at least one second extended pacing pulse vector between (1) at least one of the first left ventricular electrode and the second left ventricular electrode, and (2) a supraventricular electrode in a right atrial region commonly connected to a connector block electrode of an implantable pulse generator, and wherein delivering a pacing pulse includes delivering a pacing pulse according to the programmed second extended pacing pulse vector.

14. A method, comprising:
programming at least one first extended pacing pulse vector between (1) at least one of a first left ventricular electrode commonly connected to a second left ventricular electrode in a left ventricular region, and (2) a right ventricular electrode in a right ventricular region;
delivering a pacing pulse according to the programmed first extended pacing pulse vector;
programming at least one second extended pacing pulse vector between (1) the first and second commonly connected left ventricular electrodes, and (2) a commonly connected supraventricular electrode in a right atrial region and a connector block electrode of an implantable pulse generator; and
delivering a pacing pulse according to the programmed second extended pacing pulse vector.

15. A method, comprising:
programming at least one extended pacing pulse vector between a first right ventricular electrode in a right ventricular region and at least one of a first left ventricular electrode and a second left ventricular electrode in a left ventricular region; and
delivering a pacing pulse between the first left ventricular electrode and the second left ventricular electrode and the first right ventricular electrode and a connector block electrode of an implantable pulse generator, where the first and second left ventricular electrodes are common and the first right ventricular electrode and the connector block electrode are common.

16. A method comprising:
disposing a first electrode in association with a left ventricular region of a heart;
disposing a second electrode in association with a right atrial region of the heart;
delivering a first pacing pulse between the first and second electrodes;
disposing a connector block electrode of an implantable pulse generator in association with the heart;
delivering a second pacing pulse between the first electrode and the connector block electrode of the implantable pulse generator;
disposing a third electrode in association with the left ventricular region;
coupling the third electrode electrically in common with the first electrode; and
wherein the delivering the second pacing pulse includes delivering the second pacing pulse between (1) the commonly-connected first and third electrodes and (2) the connector block electrode of the implantable pulse generator.

17. A method comprising:
disposing a first electrode in association with a left ventricular region of a heart;
disposing a second electrode in association with a right ventricular region of the heart;
disposing a connector block electrode of an implantable pulse generator in association with the heart;
delivering a first pacing pulse between the first and second electrodes;
disposing a third electrode in association with the left ventricular region;
coupling the third electrode electrically in common with the first electrode, wherein the delivering the first pacing pulse includes delivering the pacing pulse between: (1) the commonly connected first and third electrodes; and (2) the second electrode; and
delivering a second pacing pulse between the first electrode and the connector block electrode of the implantable pulse generator.

18. The method of claim 17, wherein the delivering the second pacing pulse includes delivering the second pacing pulse between (1) the commonly-connected first and third electrodes and (2) the connector block electrode of the implantable pulse generator.

19. A method comprising:
disposing a first electrode in association with a left ventricular region of a heart;
disposing a second electrode in association with a right atrial region of the heart;
delivering a first pacing pulse between the first and second electrodes;
disposing a connector block electrode of an implantable pulse generator in association with the heart; and
delivering a second pacing pulse between the first electrode and the connector block electrode of the implantable pulse generator.

20. The method of claim 19, further comprising:
disposing a third electrode in association with the left ventricular region;
coupling the third electrode electrically in common with the first electrode; and
wherein the delivering the second pacing pulse includes delivering the second pacing pulse between (1) the commonly-connected first and third electrodes and (2) the connector block electrode of the implantable pulse generator.

21. A method comprising:
disposing first and second right ventricular electrodes in a right ventricular region;
disposing first and second left ventricular electrodes in a left ventricular region; and
programming at least one extended pacing pulse vector between commonly connected first and second right ventricular electrodes and at least one of the first left ventricular electrode or the second left ventricular electrode.

22. A method comprising:
disposing an anodic first electrode within a ventricle at or near an apex of the ventricle;
disposing a cathodic second electrode in association with the ventricle at a location that is more proximal than the first electrode; and
delivering a pacing level pulse between the anodic first electrode and the cathodic second electrode.

23. The method of claim 22, wherein the disposing the cathodic second electrode includes disposing a defibrillation electrode.

24. The method of claim 23, the disposing the cathodic second electrode includes positioning the first ventricular electrode in a right ventricular region, and wherein disposing the anodic first electrode includes positioning the first pacing/sensing electrode at or near an apex of the right ventricular region.

* * * * *